US00PP18449P2

(12) United States Plant Patent
Heinrich

(10) Patent No.: US PP18,449 P2
(45) Date of Patent: Jan. 22, 2008

(54) *ARGYRANTHEMUM* PLANT NAMED 'WESARYEL'

(50) Latin Name: *Argyranthemum frutescens*
Varietal Denomination: Wesaryel

(75) Inventor: Westhoff Heinrich, Südlohn (DE)

(73) Assignee: J. + H. Westhoff Interpel, Südlohn (DE)

( * ) Notice: Subject to any disclaimer, the term of this patent is extended or adjusted under 35 U.S.C. 154(b) by 0 days.

(21) Appl. No.: 11/513,611

(22) Filed: Aug. 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Argyranthemum* plant named 'Wesaryel', characterized by its compact, uniform, outwardly spreading and mounded plant habit; freely branching and vigorous growth habit; dark green-colored foliage; freely flowering habit; and daisy-type inflorescences with bright yellow-colored ray florets.

2 Drawing Sheets

Botanical designation: *Argyranthemum frutescens.*
Cultivar denomination: 'Wesaryel'.

BACKGROUND OF THE INVENTION

The present invention relates to a new and distinct cultivar of *Argyranthemum* plant, botanically known as *Argyranthemum frutescens* and hereinafter referred to by the name 'Wesaryel'.

The objective of the breeding program is to create new compact *Argyranthemum* cultivars with good vigor and strong branching habit, numerous inflorescences, desirable and unique floret colors, and good garden performance.

The new *Argyranthemum* originated from a cross-pollination in Südlohn, Germany of a proprietary selection of *Argyranthemum frutescens* identified as code number 03P27, not patented, as the female, or seed, parent with a proprietary selection of *Argyranthemum frutescens* identified as code number 03P17, as the male, or pollen, parent. The new *Argyranthemum* was discovered and selected by the Inventor as a single flowering plant within the progeny of the stated open-pollination in a controlled environment in Südlohn, Germany in 2004.

Asexual reproduction of the new *Argyranthemum* by vegetative tip cuttings was first conducted in Südlohn, Germany in January, 2003. Asexual reproduction by cuttings has shown that the unique features of this new *Argyranthemum* are stable and reproduced true to type in successive generations.

SUMMARY OF THE INVENTION

Plants of the cultivar Wesaryel have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Wesaryel'. These characteristics in combination distinguish 'Wesaryel' as a new and distinct potted *Argyranthemum* cultivar:

1. Compact, uniform, outwardly spreading and mounded plant habit.
2. Freely branching and vigorous growth habit.
3. Dark green-colored foliage.
4. Freely flowering habit.
5. Daisy-type inflorescences with bright yellow-colored ray florets.
6. Good garden performance.

Plants of the new *Argyranthemum* differ from plants of the female parent selection in the following characteristics:

1. Plants of the new *Argyranthemum* are more compact and have shorter internodes than plants of the female parent selection.
2. Plants of the new *Argyranthemum* are more freely flowering than plants of the female parent selection.

Plants of the new *Argyranthemum* differ from plants of the male parent selection in the following characteristics:

1. Plants of the new *Argyranthemum* are more freely flowering than plants of the male parent selection.
2. Plants of the new *Argyranthemum* have larger inflorescences than plants of the male parent selection.
3. Plants of the new *Argyranthemum* have brighter yellow-colored ray florets than plants of the male parent selection.

Plants of the new *Argyranthemum* can be compared to plants of the *Argyranthemum* cultivar Dana, not patented. In side-by-side comparisons conducted in Südlohn, Germany, plants of the new *Argyranthemum* differed from plants of the cultivar Dana in the following characteristics:

1. Plants of the new *Argyranthemum* were more compact and had shorter internodes than plants of the cultivar Dana.
2. Plants of the new *Argyranthemum* had larger leaves than plants of the cultivar Dana.

3. Inflorescences of plants of the new *Argyranthemum* had larger ray florets than plants of the cultivar Dana.
4. Plants of the new *Argyranthemum* and the cultivar Dana differed in ray floret coloration as plants of the cultivar Dana had white-colored ray florets.

Plants of the new *Argyranthemum* can be compared to plants of the *Argyranthemum* cultivar Wesarwhi, disclosed in U.S. Plant Pat. No. 17,440. In side-by-side comparisons conducted in Südlohn, Germany, plants of the new *Argyranthemum* differed from plants of the cultivar Wesarwhi in the following characteristics:

1. Plants of the new *Argyranthemum* had larger inflorescences than plants of the cultivar Wesarwhi.
2. Inflorescences of plants of the new *Argyranthemum* had more ray florets than plants of the cultivar Wesarwhi.
3. Inflorescences of plants of the new *Argyranthemum* had more phyllaries than plants of the cultivar Wesarwhi.
4. Plants of the new *Argyranthemum* and the cultivar Wesarwhi differed in ray floret coloration as plants of the cultivar Wesarwhi had white-colored ray florets.

BRIEF DESCRIPTION OF THE PHOTOGRAPHS

The accompanying photographs illustrate the overall appearance of the new *Argyranthemum*. These photographs show the colors as true as it is reasonably possible to obtain in colored reproductions of this type. Colors in the photographs may differ slightly from the color values cited in the detailed botanical description which accurately describe the colors of the new *Argyranthemum*.

The photograph on the first sheet comprises a side perspective view of a typical flowering plant of 'Wesaryel'.

The photograph on the second sheet is a close-up view of typical inflorescences of 'Wesaryel'.

DETAILED BOTANICAL DESCRIPTION

The aforementioned photographs and following observations and measurements describe plants grown during the spring and early summer in Südlohn, Germany in a glass-covered greenhouse and under conditions and practices which approximate those generally used in commercial potted *Argyranthemum* production. During the production of the plants, day temperatures ranged from 20° C. to 25° C. and night temperatures ranged from 16° C. to 18° C. Plants were pinched about three to four weeks after planting. Plants used in the photographs and for the description were about five months old. In the following description, color references are made to The Royal Horticultural Society Colour Chart, 2001 Edition, except where general terms of ordinary dictionary significance are used.

Botanical classification: *Argyranthemum frutescens* cultivar Wesaryel.

Parentage:

*Female, or seed, parent.*—Proprietary selection of *Argyranthemum frutescens* identified as code number 03P27, not patented.

*Male, or pollen, parent.*—Proprietary selection of *Argyranthemum frutescens* identified as code number 03P17, not patented.

Propagation:

*Type.*—Terminal cuttings.

*Time to initiate roots, summer.*—About seven to ten days at temperatures of about 18° C. to 20° C.

*Time to initiate roots, winter.*—About 10 to 14 days at temperatures of about 18° C. to 20° C.

*Time to produce a rooted young plant, summer.*—About 15 to 20 days at temperatures of about 18° C. to 20° C.

*Time to produce a rooted young plant, winter.*—About 18 to 21 days at temperatures of about 18° C. to 20° C.

*Root description.*—Fine, fibrous.

*Rooting habit.*—Freely branching.

Plant description:

*Appearance.*—Herbaceous daisy-type potted *Argyranthemum*. Compact, uniform, outwardly spreading and mounded plant habit. Strong and freely branching growth habit with lateral branches potentially developing at every node; dense and full plants. Vigorous growth habit.

*Plant height.*—About 30 cm.

*Plant width.*—About 26.5 cm.

*Lateral branches.*—Diameter: About 4 mm. Internode length: About 1 cm. Strength: Strong; young stems, flexible. Texture: Young stems, smooth, glabrous; older stems, woody. Color: Young stems: Between 146C and 146D. Older stems: Between 147B and 147C overlain with 199A.

Foliage description:

*Arrangement.*—Alternate, simple; sessile.

*Length.*—About 8.8 cm.

*Width.*—About 4.8 cm.

*Apex.*—Acute.

*Base.*—Attenuate.

*Margin.*—Pinnatifid; serrate.

*Texture, upper and lower surfaces.*—Smooth, glabrous.

*Color.*—Developing foliage, upper surface: 137B. Developing foliage, lower surface: 137C. Fully expanded foliage, upper surface: 137A; venation, 137C. Fully expanded foliage, lower surface: 137C; venation, 137C.

Inflorescence description:

*Appearance.*—Daisy-type inflorescence form with elongated oblong to broadly ligulate-shaped ray florets. Inflorescences borne on terminals above foliage. Disk and ray florets arranged acropetally on a capitulum. Inflorescences not fragrant.

*Flowering season.*—Plants flower from spring to early fall in Germany; flowering continuous during this period.

*Inflorescence longevity.*—Inflorescences last about 20 days on the plant; inflorescences persistent.

*Quantity of inflorescences.*—Freely flowering, about 40 inflorescences per plant.

*Inflorescence bud.*—Height: About 4 mm. Diameter: About 7 mm. Shape: Oblate. Color: Towards the apex, 195B; towards the base, 144A.

*Inflorescence size.*—Diameter: About 5.7 cm. Depth (height): About 8 mm. Diameter of disc: About 1.5 cm. Receptacle height: About 3.5 mm. Receptacle diameter: About 1.3 cm.

*Ray florets.*—Shape: Elongated-oblong to broadly ligulate. Orientation: Initially upright, then about 90° from vertical or perpendicular to peduncle. Length: About 2.2 cm. Width: About 9 mm. Apex: Obtuse or emarginate. Base: Obtuse. Margin: Entire. Texture, upper and lower surfaces: Smooth, glabrous, satiny. Number of ray florets per inflorescence: About 20 arranged in a single whorl. Color: When opening, upper surface: Between 5A and 6A. When opening, lower surface: 6C. Fully opened, upper surface: 5A; color becoming closer to 5C with development. Fully opened, lower surface: 6D.

*Disc florets.*—Arrangement: Massed at center of receptacle. Shape: Tubular, elongated. Apex: Five-pointed. Length: About 4.5 mm. Width, at apex: About 2 mm. Width, at base: About 0.9 mm. Number of disc florets per inflorescence: About 245. Color: Immature: 15A. Mature: Apex: 15B. Mid-section: Between 145C and 145D. Base: 145B.

*Phyllaries.*—Number of phyllaries per inflorescence: About 35. Length: About 4 mm. Width: About 2 mm. Shape: Elliptic to ovate. Apex: Acute. Base: Truncate. Margin: Entire. Texture, upper and lower surfaces: Smooth, glabrous; margins, papery. Color, upper and lower surfaces: Between 146A and 146D overlain with between 199B and 199D.

*Peduncles.*—Length: About 5.3 cm. Diameter: About 1.9 mm. Angle: About 45° from vertical. Strength: Strong, flexible. Texture: Smooth, glabrous. Color: Between 13A and 137B.

*Reproductive organs.*—Androecium: Present on disc florets only. Anther length: Less than 1 mm. Anther shape: Ovoid. Anther color: 15A. Pollen amount: None observed. Gynoecium: Present on both ray and disc florets. Pistil length: About 5.5 mm. Stigma shape: Two-parted. Stigma color: 15B. Style length: About 3 mm. Style color: 15D overlain with N144B. Ovary color: Between 145C and 145D.

*Seed/fruit.*—Seed and fruit production has not been observed.

Disease/pest resistance: Resistance to pathogens and pests common to *Argyranthemums* has not been observed on plants grown under commercial conditions.

Garden performance: Plants of the new *Argyranthemum* have been observed to have good garden performance and to tolerate wind, rain and temperatures from about 2° C. to about 30° C.

It is claimed:

1. A new and distinct *Argyranthemum* plant named 'Wesaryel' as illustrated and described.

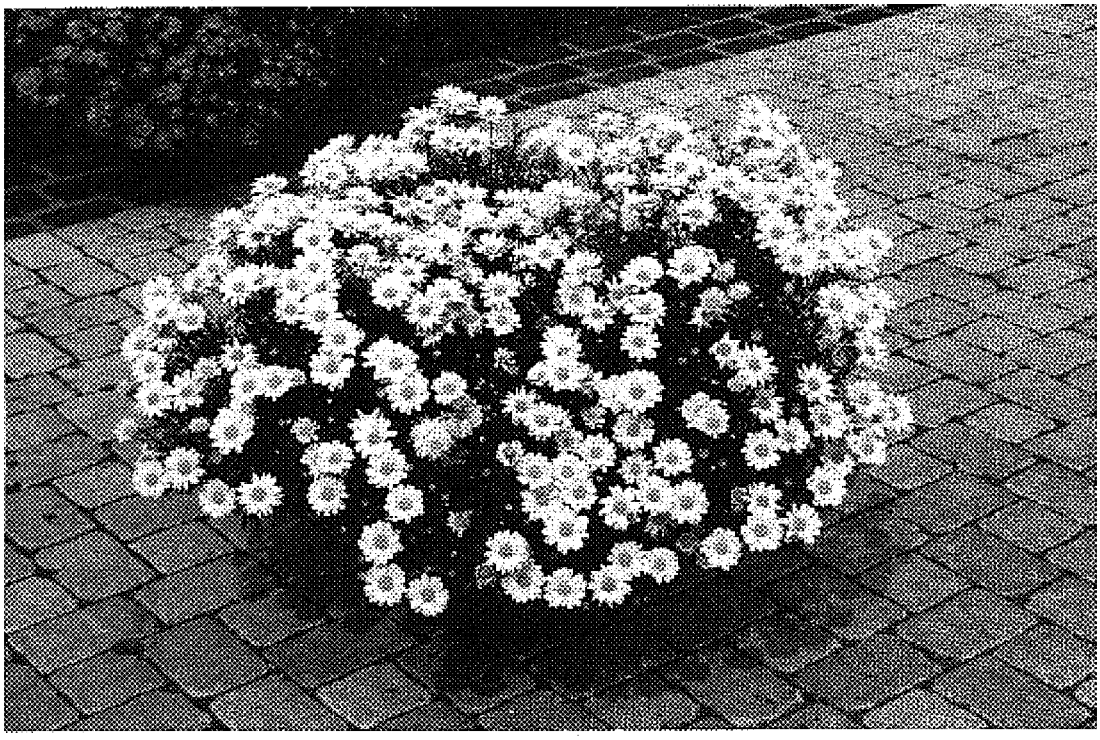

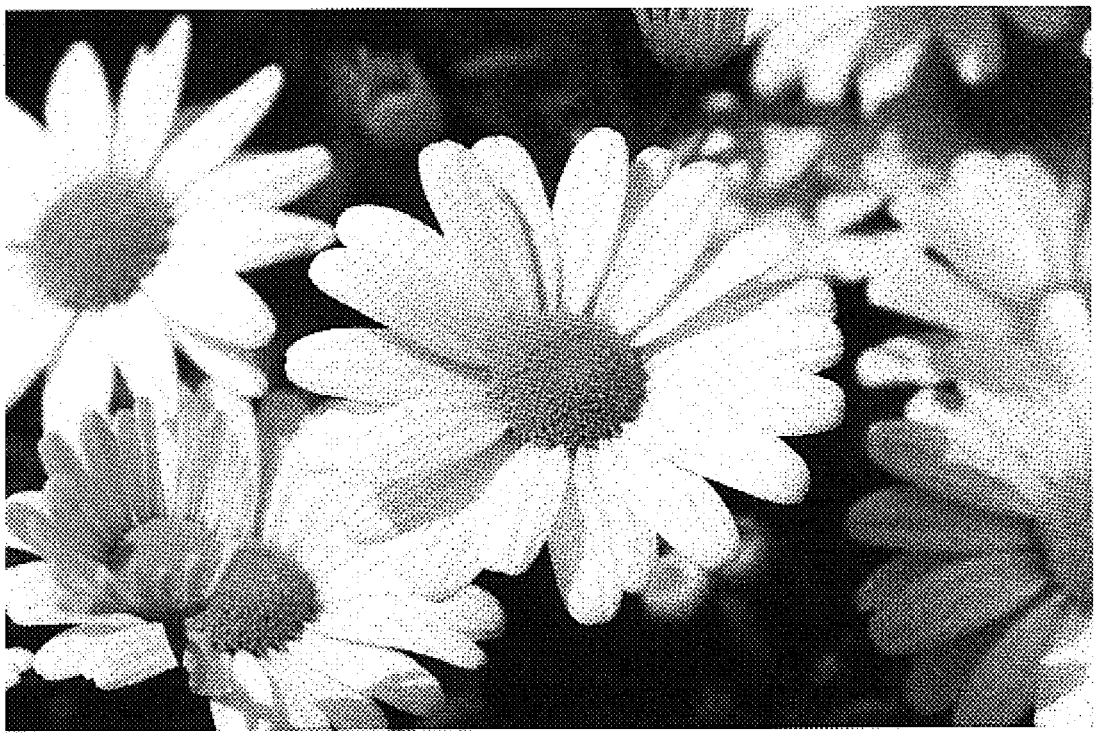

* * * * *